(12) United States Patent
Ghaffari et al.

(10) Patent No.: US 11,147,493 B2
(45) Date of Patent: Oct. 19, 2021

(54) NON-INVASIVE DETECTION OF CORONARY ARTERY DISEASE

(71) Applicants: Ali Ghaffari, Tehran (IR); Seyyed Abbas Atyabi, Tehran (IR); Mohammadmehdi Daevaeiha, Tehran (IR)

(72) Inventors: Ali Ghaffari, Tehran (IR); Seyyed Abbas Atyabi, Tehran (IR); Mohammadmehdi Daevaeiha, Tehran (IR)

(*) Notice: Subject to any disclaimer, the term of this patent is extended or adjusted under 35 U.S.C. 154(b) by 150 days.

(21) Appl. No.: 16/686,162

(22) Filed: Nov. 17, 2019

(65) Prior Publication Data

US 2020/0077911 A1 Mar. 12, 2020

Related U.S. Application Data

(60) Provisional application No. 62/768,915, filed on Nov. 18, 2018.

(51) Int. Cl.
*A61B 5/00* (2006.01)
*A61B 5/316* (2021.01)
*A61B 5/366* (2021.01)

(52) U.S. Cl.
CPC ............. *A61B 5/316* (2021.01); *A61B 5/366* (2021.01); *A61B 5/726* (2013.01)

(58) Field of Classification Search
CPC . A61B 5/316; A61B 5/318; A61B 5/346–366; A61B 5/72–726; A61B 5/726; A61B 5/282
See application file for complete search history.

(56) References Cited

U.S. PATENT DOCUMENTS

| | | | |
|---|---|---|---|
| 2014/0005988 A1* | 1/2014 | Brockway | A61B 5/349 703/2 |
| 2016/0022164 A1* | 1/2016 | Brockway | A61B 5/726 600/509 |

* cited by examiner

*Primary Examiner* — Scott M. Getzow
(74) *Attorney, Agent, or Firm* — Bajwa IP Law Firm; Haris Zaheer Bajwa

(57) ABSTRACT

A method for non-invasive detection of coronary artery disease (CAD). The method includes acquiring a raw ECG signal from a patient, generating a denoised ECG signal by applying a first wavelet transform on the raw ECG signal, generating an artifact-free ECG signal by applying a second wavelet transform on the denoised ECG signal, generating a filtered ECG signal by applying a band-stop filter on the artifact-free ECG signal, extracting an averaged ECG signal of a plurality of averaged ECG signals from the filtered ECG signal, detecting an ST segment in the averaged ECG signal by applying a delineation algorithm on the averaged ECG signal, detecting an isoelectric line in the averaged ECG signal, determining an existence of CAD in the patient responsive to detecting a CAD detection condition, and determining a non-existence of CAD responsive to not detecting the CAD detection condition.

20 Claims, 15 Drawing Sheets

NON-INVASIVE DETECTION OF CORONARY ARTERY DISEASE

CROSS-REFERENCE TO RELATED APPLICATION

This application claims the benefit of priority from U.S. Provisional Patent Application Ser. No. 62/768,915, filed on Nov. 18, 2018, and entitled "A NOVEL SYSTEM AND APPARATUS FOR TIMELY AND NONINVASIVE DETECTION OF CORONARY ARTERY DISEASE (CAD) ONLY BY INTELLIGENT ANALYSIS OF ELECTROCARDIOGRAM (ECG)," which is incorporated herein by reference in its entirety.

TECHNICAL FIELD

The present disclosure generally relates to signal processing, and particularly, to biomedical signal processing.

BACKGROUND

Heart diseases are, generally, a leading cause of death worldwide. Coronary artery diseases (CADs) are among major heart diseases that cause myocardial ischemia and myocardial infarction (MI). A major cause of heart attack is a blockage of blood flow to heart muscles, caused by a damage or disease in a heart's major blood vessels (coronary arteries). Before an occurrence of a heart attack, a heart's myocyte may experience lack of enough oxygen due to a blockage of blood flow. A phase before an onset of any necrosis in myocyte and an occurrence of MI is called ischemia. Early detection of ischemia may be crucial because in most cases, effects of myocardial ischemia may be reversible if detected early enough. Myocardial ischemia is commonly seen as a warning sign of cardiac problems. Therefore, it may be beneficial for patients and cardiologists to be able to recognize signs and symptoms of ischemia before a permanent cardiac tissue death.

Electrocardiography (ECG) has been a major cardiovascular diagnostic tool. In spite of a rapid progress in development of new hardware and software approaches for ECG detection, cardiologists still mainly rely on direct visual assessment of ECG signals. However, in many myocardial ischemia cases such as silent ischemia and stable coronary heart disease, no specific changes may be observed in ECG, and therefore, due to a lack of diagnostic accuracy and frequent false alarms in ECG interpretation, electrocardiographic-based analysis of such patients may not be deemed reliable enough for cardiologists. There is, therefore, a need for a method for early detection of CAD by processing ECG signals that may include no observable change compared to normal ECG signals.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

In one general aspect, the present disclosure describes an exemplary method for non-invasive detection of coronary artery disease (CAD). An exemplary method may include acquiring a raw electrocardiography (ECG) signal from a patient, generating a denoised ECG signal by applying a first wavelet transform on the raw ECG signal, generating an artifact-free ECG signal by applying a second wavelet transform on the denoised ECG signal, generating a filtered ECG signal by applying a finite impulse response (FIR) filter on the artifact-free ECG signal, extracting an averaged ECG signal of a plurality of averaged ECG signals from the filtered ECG signal, detecting an ST segment and an isoelectric line in the averaged ECG signal, determining an existence of CAD in the patient responsive to detecting at least one of a plurality of CAD detection conditions, and determining a non-existence of CAD responsive to not detecting the at least one of the plurality of CAD detection conditions. An exemplary filtered ECG signal may include a plurality of QRS complexes.

In an exemplary embodiment, detecting the at least one of a plurality of CAD detection conditions may include detecting one of a depression or an elevation in the ST segment with respect to the isoelectric line, detecting a deformation in the ST segment, or detecting a plurality of abnormal morphologies in the plurality of averaged ECG signals.

In an exemplary embodiment, acquiring the raw ECG signal may include placing three precordial ECG leads on a chest of the patient and recording the raw ECG signal from the three precordial ECG leads.

In an exemplary embodiment, extracting the averaged ECG signal may include extracting five consecutive QRS complexes of the plurality of QRS complexes from the filtered ECG signal.

In an exemplary embodiment, detecting the one of the depression or the elevation in the ST segment may include measuring variations of the ST segment with respect to the isoelectric line, defining a first membership function associated with the variations of the ST segment, calculating a first membership value for the ST segment utilizing the first membership function, and determining an existence of the one of the depression or the elevation in the ST segment responsive to the first membership value being equal to or higher than a first threshold.

In an exemplary embodiment, detecting the deformation in the ST segment may include detecting a T-wave and an initial J-point in the averaged ECG signal, measuring a difference between the initial J-point and the isoelectric line, defining a second membership function associated with the difference, calculating a second membership value for the difference utilizing the second membership function, and determining an existence of the deformation in the ST segment responsive to the second membership function being equal to or larger than a second threshold. In an exemplary embodiment, detecting the T-wave may include detecting a type of the T-wave. An exemplary type of the T-wave may include one of a normal T-wave and an inverted T-wave.

An exemplary method may further include determining a modified J-point on the averaged ECG signal responsive to detecting the inverted T-wave by modifying a location of the initial J-point on the averaged ECG signal and replacing the initial J-point with the modified J-point prior to measuring the difference between the initial J-point and the isoelectric line.

In an exemplary embodiment, detecting the plurality of abnormal morphologies may include detecting each of the plurality of abnormal morphologies in a respective averaged ECG signal of the plurality of averaged ECG signals. In an exemplary embodiment, detecting each of the plurality of abnormal morphologies may include detecting an averaged QRS complex in the respective averaged ECG signal, detecting an S-wave and an R-wave in the averaged QRS complex, detecting an averaged J-point in the respective averaged ECG signal based on the S-wave and the R-wave, extracting an updated QRS complex from the averaged QRS complex based on the averaged J-point, calculating a number of edges in the updated QRS complex, and determining an existence of an abnormal morphology of the plurality of abnormal morphologies in the respective averaged ECG signal responsive to a temporal duration of the updated QRS complex being less than a temporal threshold and the number of edges being larger than a lower limit.

In an exemplary embodiment, detecting the plurality of abnormal morphologies may include detecting the plurality of abnormal morphologies in at least 25% of the plurality of averaged ECG signals. In an exemplary embodiment, the plurality of averaged ECG signals may include a duration of at least 10 minutes.

Other exemplary systems, methods, features and advantages of the implementations will be, or will become, apparent to one of ordinary skill in the art upon examination of the following figures and detailed description. It is intended that all such additional systems, methods, features and advantages be included within this description and this summary, be within the scope of the implementations, and be protected by the claims herein.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

In the following detailed description, numerous specific details are set forth by way of examples in order to provide a thorough understanding of the relevant teachings. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be readily apparent to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

Herein is disclosed an exemplary method and system for non-invasive detection of coronary artery disease (CAD). An exemplary method acquires raw electrocardiography (ECG) signals from a patient and after preprocessing acquired signals, extracts averaged ECG signals from the raw data. Exemplary averaged ECG signals include data of consecutive heartbeats that may be averaged over one heartbeat period. The averaged ECG signal may then be processed to extract different features from the signal, including a QRS complex, an ST segment, and signal morphology. Based on a fuzzy decision making technique, the extracted features may be analyzed to detect a CAD detection condition, such as an elevation/depression in the ST segment, a deformation in the ST segment, or an abnormal morphology in the QRS complex. This process may be repeated on several parts of the raw ECG signal and if the CAD detection conditions are detected in a considerable portion of acquired data (i.e., a number of detections exceeds a given threshold), CAD may be detected based on the ECG signal. Otherwise, the acquired ECG signal may be considered normal.

Figure 1A:
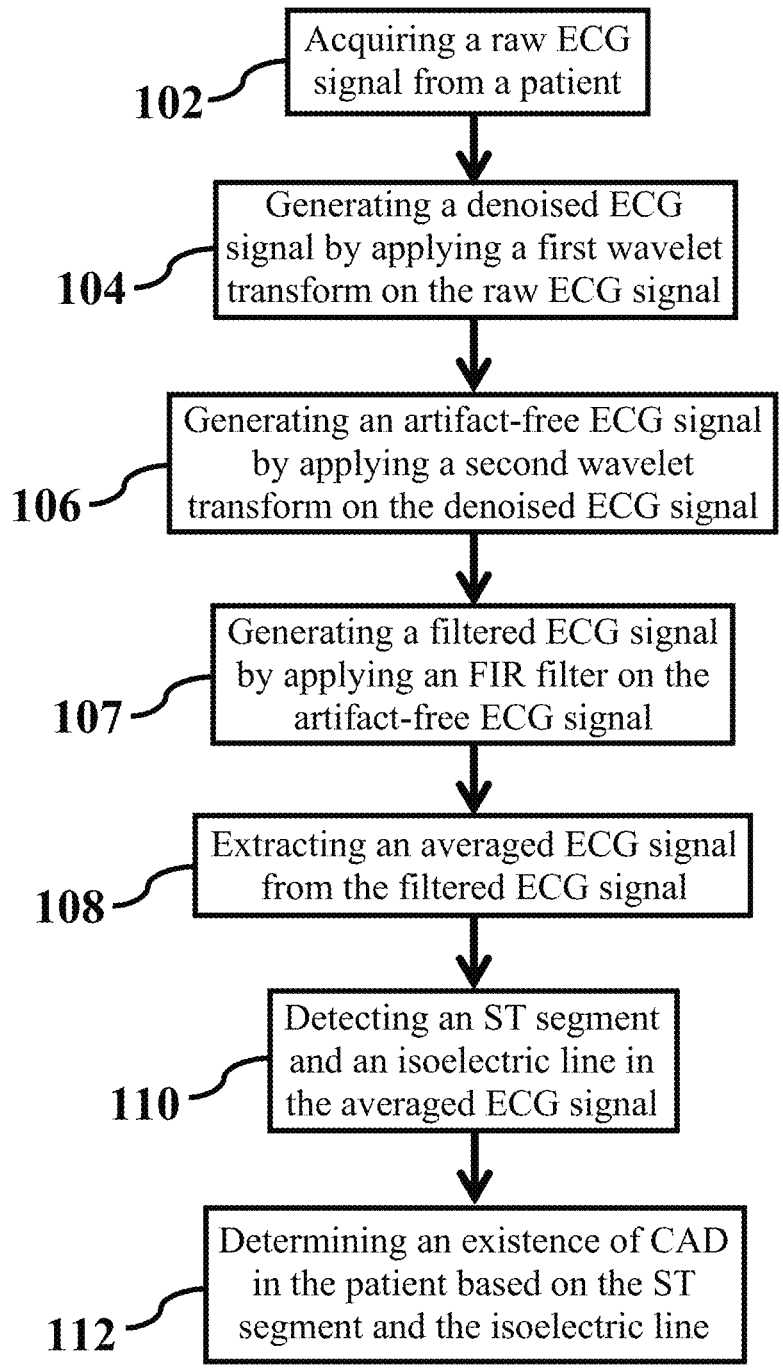
FIG. 1A shows a flowchart of a method for non-invasive detection of coronary artery disease (CAD), consistent with one or more exemplary embodiments of the present disclosure.

FIG. 1A shows a flowchart of a method for non-invasive detection of CAD, consistent with one or more exemplary embodiments of the present disclosure. An exemplary method 100 may include acquiring a raw electrocardiography (ECG) signal from a patient (step 102), generating a denoised ECG signal by applying a first wavelet transform on the raw ECG signal (step 104), generating an artifact-free ECG signal by applying a second wavelet transform on the denoised ECG signal (step 106), generating a filtered ECG signal by applying a band-stop filter on the artifact-free ECG signal (step 107), extracting an averaged ECG signal of a plurality of averaged ECG signals from the filtered ECG signal (step 108), detecting an ST segment and an isoelectric line in the averaged ECG signal (step 110), and determining an existence of CAD in the patient based on the ST segment and the isoelectric line (step 112).

Figure 2:
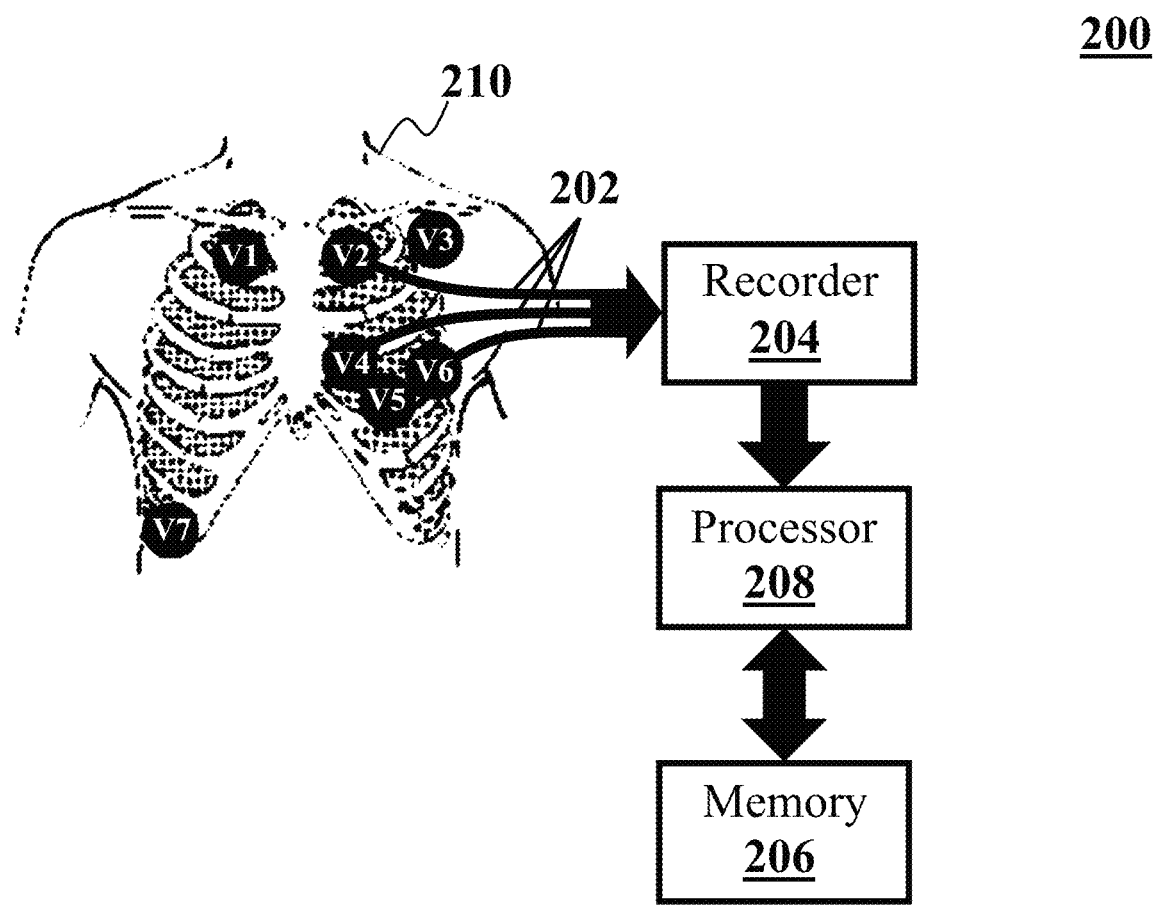
FIG. 2 shows a schematic of a system for non-invasive detection of CAD, consistent with one or more exemplary embodiments of the present disclosure.

FIG. 2 shows a schematic of a system for non-invasive detection of CAD, consistent with one or more exemplary embodiments of the present disclosure. In an exemplary embodiment, different steps of method 100 may be implemented by utilizing an exemplary system 200. An exemplary system 200 may include a plurality of ECG leads 202, an ECG recorder 204, a memory 206, and a processor 208. In an exemplary embodiment, plurality of ECG leads 202 may be placed on a chest of a patient 210.

Figure 1B:
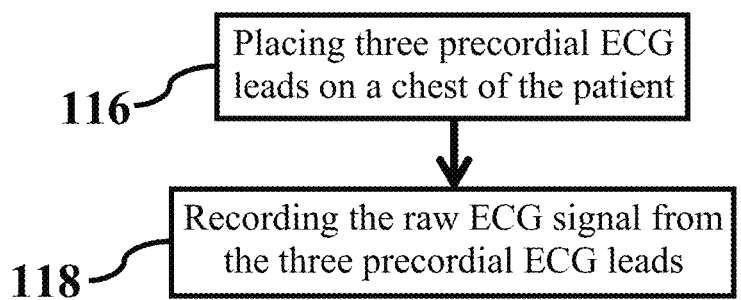
FIG. 1B shows a flowchart for acquiring a raw ECG signal from a patient, consistent with one or more exemplary embodiments of the present disclosure.

In further detail with respect to step 102, FIG. 1B shows a flowchart for acquiring a raw ECG signal from a patient, consistent with one or more exemplary embodiments of the present disclosure. In an exemplary embodiment, acquiring the raw ECG signal (step 102) may include placing three precordial ECG leads on the chest of the patient (step 116) and recording the raw ECG signal from the three precordial ECG leads (step 118).

For further detail regarding step 116, in an exemplary embodiment, plurality of ECG leads 202 may include three precordial ECG leads. Referring again to FIG. 2, the three precordial ECG leads may include ECG leads V2, V4, and V6. In an exemplary embodiment, seven electrodes (represented by V1-V7 in FIG. 2) may be placed on the chest of patient 210 for recording the three precordial ECG leads.

Figure 3A:
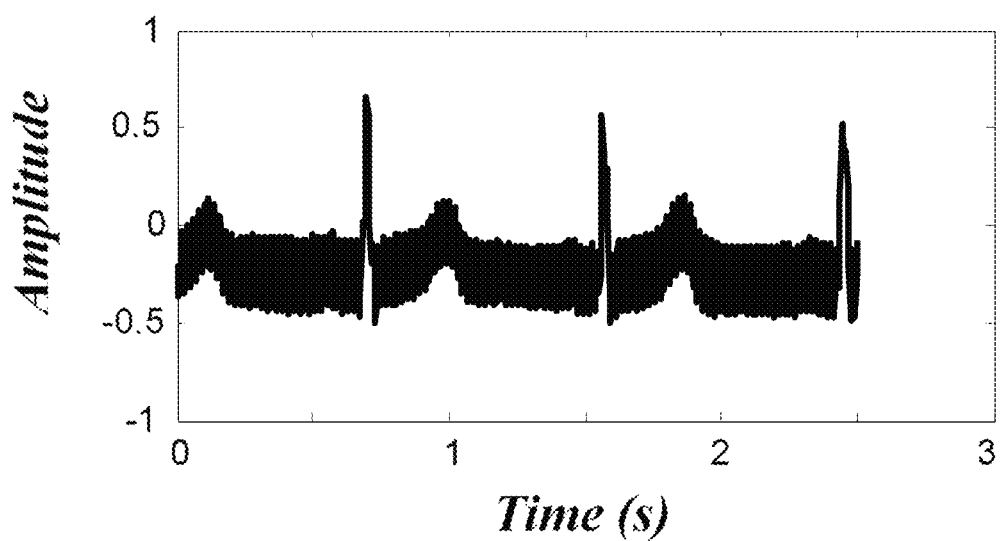
FIG. 3A shows a raw ECG signal, consistent with one or more exemplary embodiments of the present disclosure.

In further detail with regards to step 118, FIG. 3A shows a raw ECG signal, consistent with one or more exemplary embodiments of the present disclosure. In an exemplary embodiment, ECG recorder 204 may be utilized for recording a raw ECG signal 302. An exemplary ECG recorder may include a three-lead Holter monitor. In an exemplary embodiment, ECG recorder 204 may send raw ECG signal 302 to processor 208 to process raw ECG signal 302 according to steps 104-112 of method 100. In an exemplary embodiment, different steps of method 100 may be stored in memory 206 to be accessed and executed by processor 208.

Figure 3B:
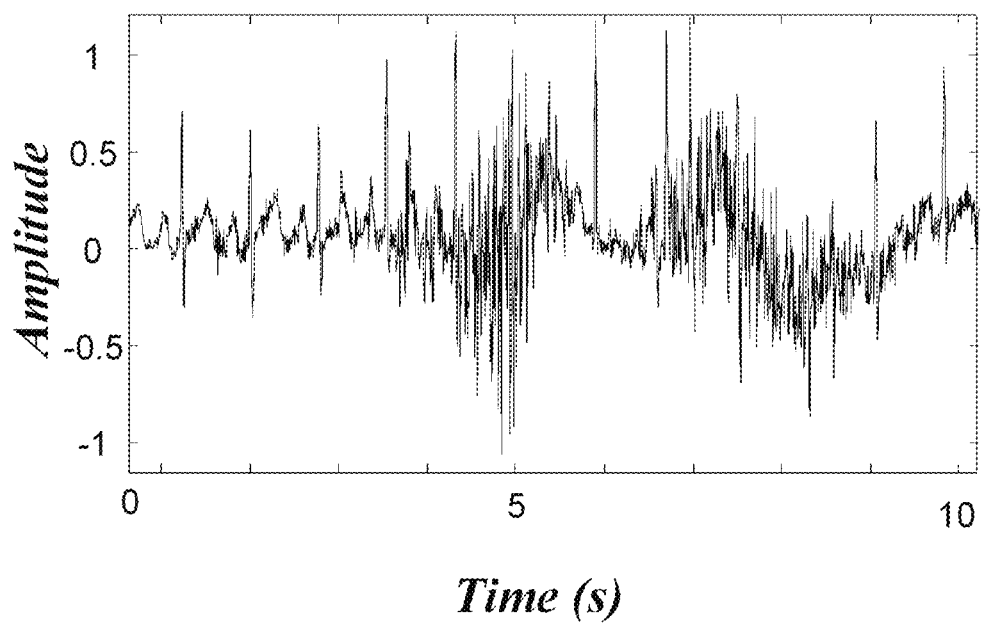
FIG. 3B shows a denoised ECG signal, consistent with one or more exemplary embodiments of the present disclosure.

Referring again to FIG. 1A, in an exemplary embodiment, step 104 may include generating a denoised ECG signal by applying a first wavelet transform on raw ECG signal 302. FIG. 3B shows a denoised ECG signal, consistent with one or more exemplary embodiments of the present disclosure. In an exemplary embodiment, the first wavelet transform may include a discrete wavelet transform. In an exemplary embodiment, noises of wavelet coefficients may be estimated by applying a discrete wavelet transform at on raw ECG signal 302. Then, by defining an appropriate threshold level, the noises may be removed and an exemplary denoised ECG signal 304 may be obtained.

Figure 3C:
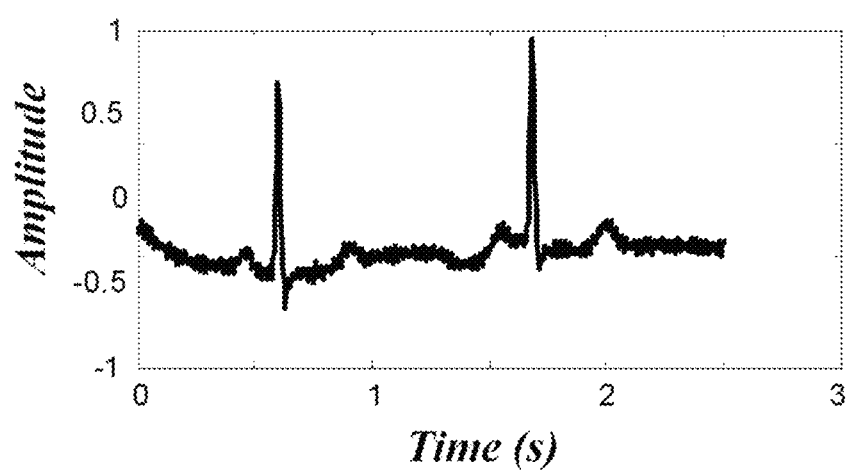
FIG. 3C shows an artifact-free ECG signal, consistent with one or more exemplary embodiments of the present disclosure.

In an exemplary embodiment, step 106 may include generating an artifact-free ECG signal by applying a second wavelet transform on denoised ECG signal 304. FIG. 3C shows an artifact-free ECG signal, consistent with one or more exemplary embodiments of the present disclosure. In an exemplary embodiment, the second wavelet transform may include a discrete wavelet transform. In an exemplary embodiment, artifact locations may be estimated by applying a discrete wavelet transform on denoised ECG signal 304. Exemplary artifacts may be a result of patient's motion or contacting with vibrating or electrical tools. In an exemplary embodiment, a sliding window may be moved on denoised ECG signal 304 and a discrete wavelet transform may be applied on a segment of denoised ECG signal 304 that is inside the sliding window. Then, noises of wavelet coefficients may be estimated. Next, by comparing obtained noise level with a proper threshold, the quality of the segment inside the sliding window is evaluated. If the noise level is above the threshold, an artifact may be identified within the segment. In an exemplary embodiment, this process may continue until the end of denoised ECG signal 304 and artifact locations may be identified throughout denoised ECG signal 304. Then, by selecting segments without any identified artifact, an exemplary artifact-free ECG signal 306 may be obtained.

Figure 3D:
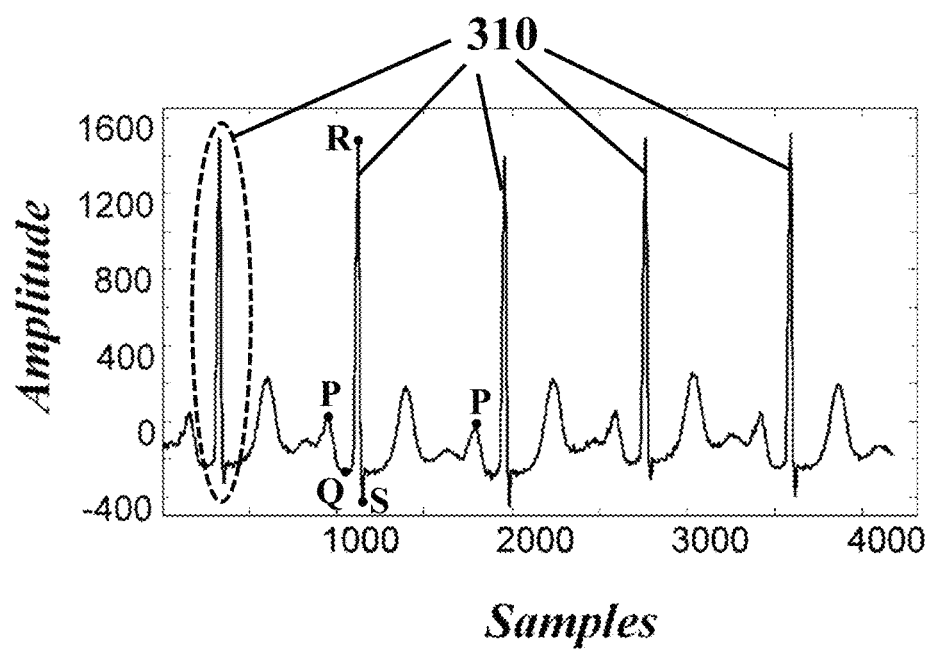
FIG. 3D shows a filtered ECG signal, consistent with one or more exemplary embodiments of the present disclosure.

In an exemplary embodiment, step 107 may include generating a filtered ECG signal by applying an FIR filter on artifact-free ECG signal 306. FIG. 3D shows a filtered ECG signal, consistent with one or more exemplary embodiments of the present disclosure. In an exemplary embodiment, the FIR filter may include a band-stop filter that may be applied on artifact-free ECG signal 306 to remove certain frequency related noises, such as power line noises in a range of bout 48-51 Hz. In an exemplary embodiment, the FIR filter may further include a high pass filter that may be applied on artifact-free ECG signal 306 to eliminate low-frequency noises. By applying the FIR filter on artifact-free ECG signal 306, an exemplary filtered ECG signal 308 may be obtained. In an exemplary embodiment, filtered ECG signal 308 may include a plurality of QRS complexes 310. An exemplary QRS complex of plurality of QRS complexes 310 may include Q, R, and S edges.

Figure 3E:
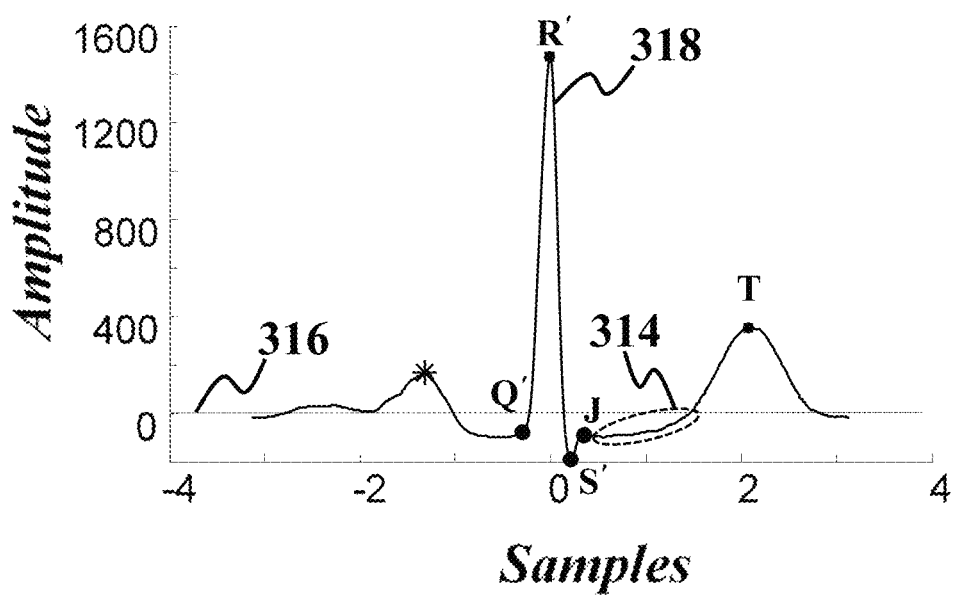
FIG. 3E shows an averaged ECG signal, consistent with one or more exemplary embodiments of the present disclosure.

In an exemplary embodiment, step 108 may include extracting an averaged ECG signal from filtered ECG signal 308. FIG. 3E shows an averaged ECG signal, consistent with one or more exemplary embodiments of the present disclosure. Extracting an exemplary averaged ECG signal 312 may include extracting five consecutive QRS complexes of plurality of QRS complexes 310 from filtered ECG signal 308. In an exemplary embodiment, each of the five consecutive QRS complexes may be delineated by applying a stationary wavelet transform (SWT, also known as a'trous discrete wavelet transform) on filtered ECG signal 308. Each exemplary QRS complex may correspond to a heartbeat pulse that may be located between onsets of two exemplary consecutive P-waves in filtered ECG signal 308. In an exemplary embodiment, a respective onset of each P-wave may be detected in filtered ECG signal 308 similar to delineating an associated QRS complex. Next, five exemplary consecutive heartbeat pulses (each being located between two successive P-wave onsets) may be extracted from filtered ECG signal 308 and averaged to obtain an exemplary averaged ECG signal 310. As a result, in an exemplary embodiment, remaining noises in filtered ECG signal 308 may be considerably removed in averaged ECG signal 312. Referring to FIGS. 3D and 3E, in an exemplary embodiment, averaged ECG signal 312 may be smoother than filtered ECG signal 308.

Referring again to FIG. 1A, in an exemplary embodiment, step 110 may include detecting an ST segment 314 and an isoelectric line 316 in averaged ECG signal 312. In an exemplary embodiment, ST segment 314 may refer to a segment in averaged ECG signal 312 between an averaged QRS complex 318 and a T-wave. In an exemplary embodiment, isoelectric line 316 may refer to a baseline of averaged ECG signal 312 where the signal has zero amplitude. In an exemplary embodiment, ST segment 314 and isoelectric line 316 may be detected by applying an SWT on averaged ECG signal 312, similar to the aforementioned delineation processes.

Figure 1C:
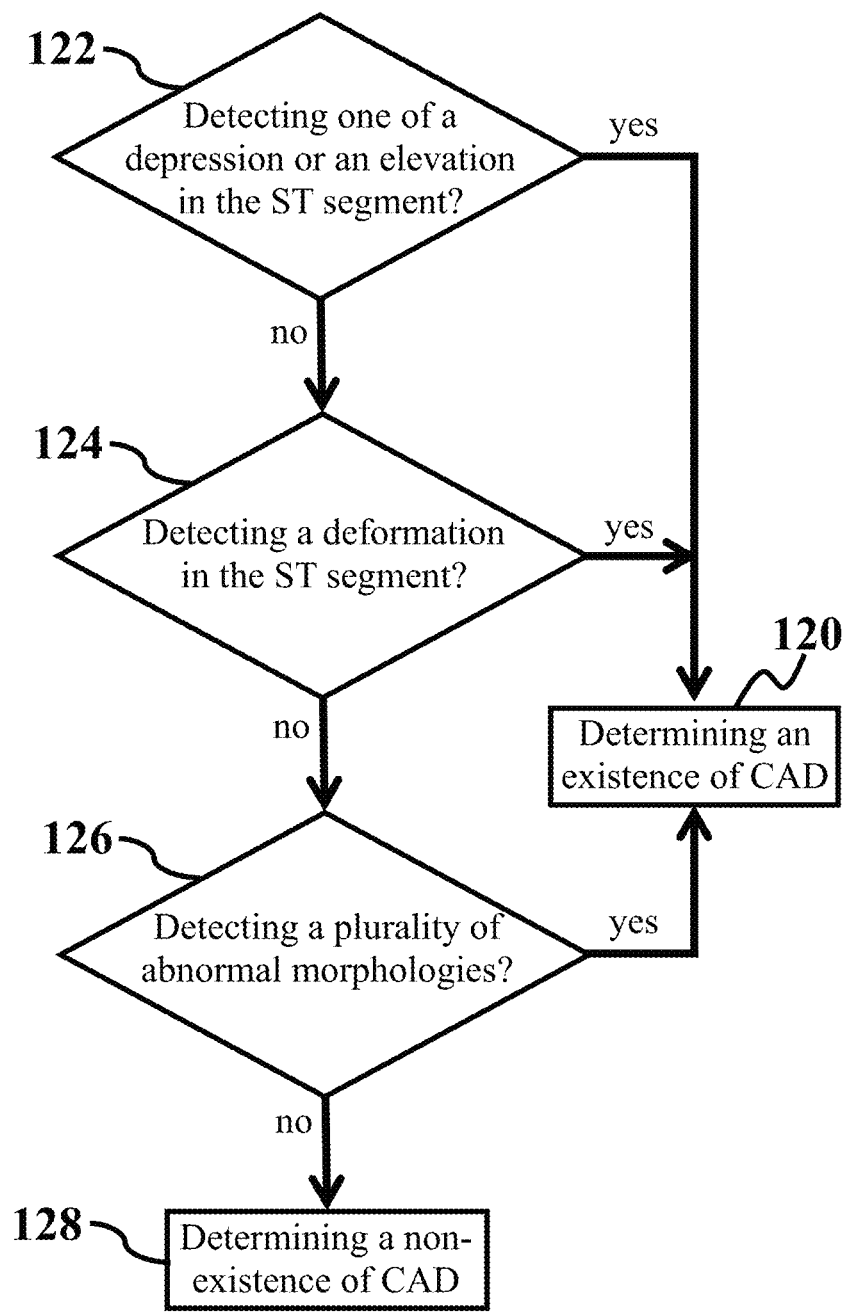
FIG. 1C shows a flowchart for determining an existence of CAD in a patient based on an ST segment and an isoelectric line, consistent with one or more exemplary embodiments of the present disclosure.

For further detail with respect to step 112, FIG. 1C shows a flowchart for determining an existence of CAD in a patient based on an ST segment and an isoelectric line, consistent with one or more exemplary embodiments of the present disclosure. In an exemplary embodiment, step 112 may include determining an existence of CAD in patient 210 (step 120) responsive to detecting at least one of a plurality of CAD detection conditions (steps 122, 124, or 126, yes), and determining a non-existence of CAD (step 128) responsive to not detecting the at least one of the plurality of CAD detection conditions (steps 122, 124, and 126).

In an exemplary embodiment, detecting the at least one of a plurality of CAD detection conditions may include detecting one of a depression or an elevation in ST segment 314 with respect to isoelectric line 316 (step 122, yes), detecting a deformation in ST segment 314 (step 124, yes), or detecting a plurality of abnormal morphologies in the plurality of averaged ECG signals (step 126, yes).

Figure 1D:
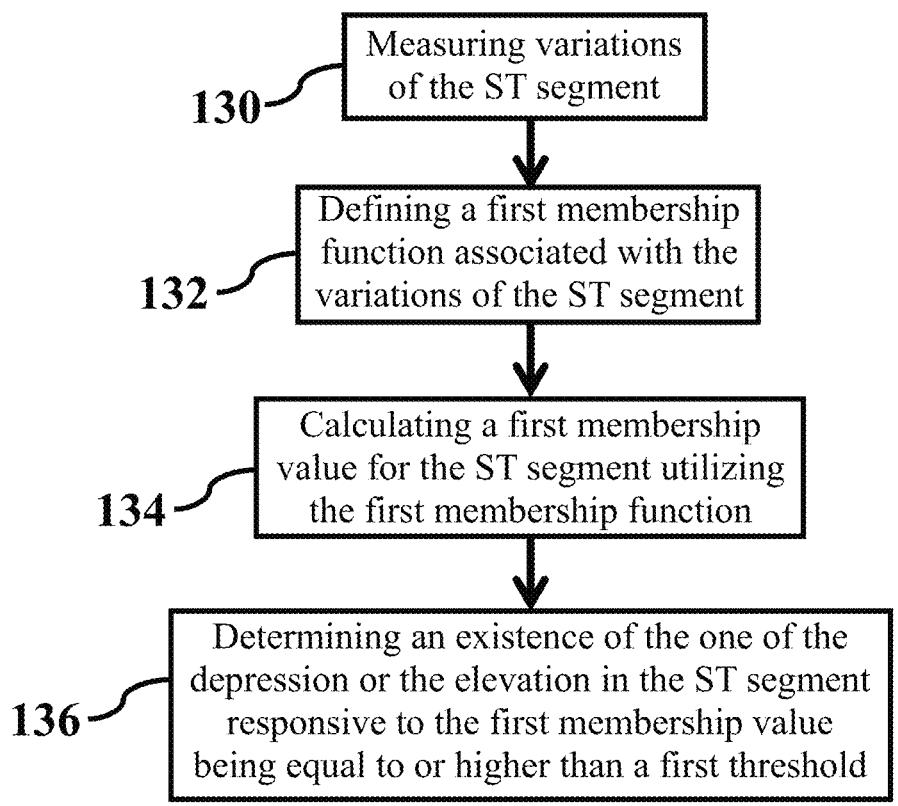
FIG. 1D shows a flowchart for detecting one of a depression or an elevation in an ST segment, consistent with one or more exemplary embodiments of the present disclosure.

In further detail regarding step 122, FIG. 1D shows a flowchart for detecting one of a depression or an elevation in an ST segment, consistent with one or more exemplary embodiments of the present disclosure. In an exemplary embodiment, step 122 may include measuring variations of ST segment 314 with respect to isoelectric line 316 (step 130), defining a first membership function associated with the variations of the ST segment (step 132), calculating a first membership value for the ST segment utilizing the first membership function (step 134), and determining an existence of the one of the depression or the elevation in the ST segment responsive to the first membership value being equal to or higher than a first threshold (step 136).

For further detail with respect to step 130, variations of an exemplary ST segment may include a depression or an elevation. In an exemplary embodiment, a depression may refer to a decrease of an ST segment's amplitude below an associated isoelectric line and an elevation may refer to an increase of an ST segment's amplitude above an associated isoelectric line. For example, referring to FIG. 3E, the variations of ST segment 314 include a depression since ST segment 314 lies below isoelectric line 316. In an exemplary embodiment, measuring ST segment 314 variations may include calculating an average of ST segment 314 variations with respect to isoelectric line 316.

Figure 4:
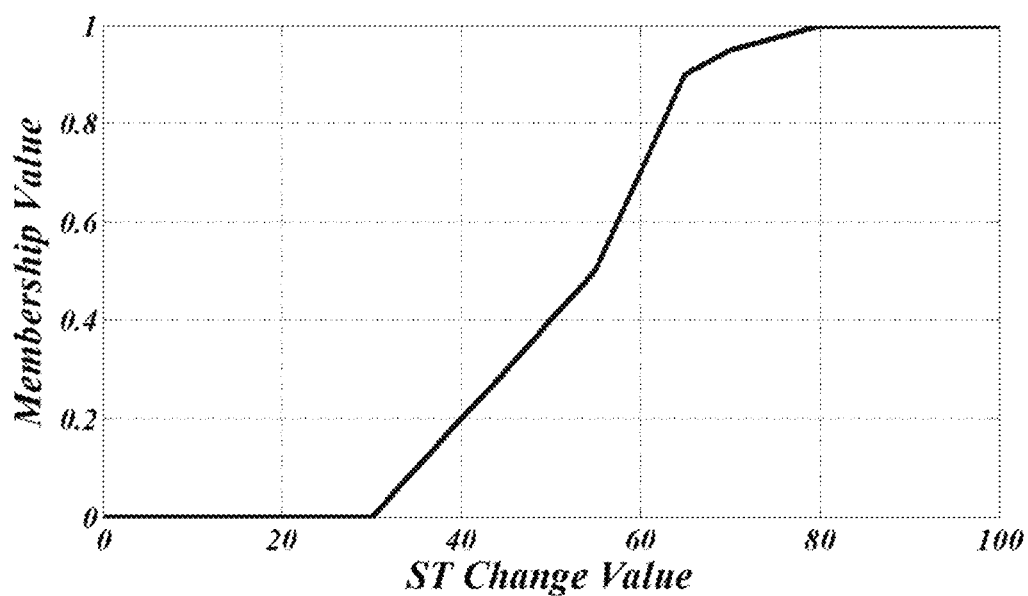
FIG. 4 shows a diagram of a first membership function, consistent with one or more exemplary embodiments of the present disclosure.

In further detail with regards to step 132, FIG. 4 shows a diagram of a first membership function, consistent with one or more exemplary embodiments of the present disclosure. An exemplary first membership function 400 may be utilized for fuzzy decision making over the variations of ST segment 314. In an exemplary embodiment, first membership function 400 may be obtained empirically by applying different functions on ST segment 314.

For further detail with respect to step 134, calculating the first membership value may include applying a measured value of variations of ST segment 314 to first membership function 400 and extracting a corresponding output of first membership function 400 as the first membership value for ST segment 314.

In further detail regarding step 136, in an exemplary embodiment, the first membership value may be compared with a first threshold. An exemplary first threshold may be set equal to about 0.8 based on examining different threshold values. In an exemplary embodiment, if the first membership value is equal to or larger than the first threshold, an existence of a depression or an elevation may be determined in ST segment 314.

Figure 1E:
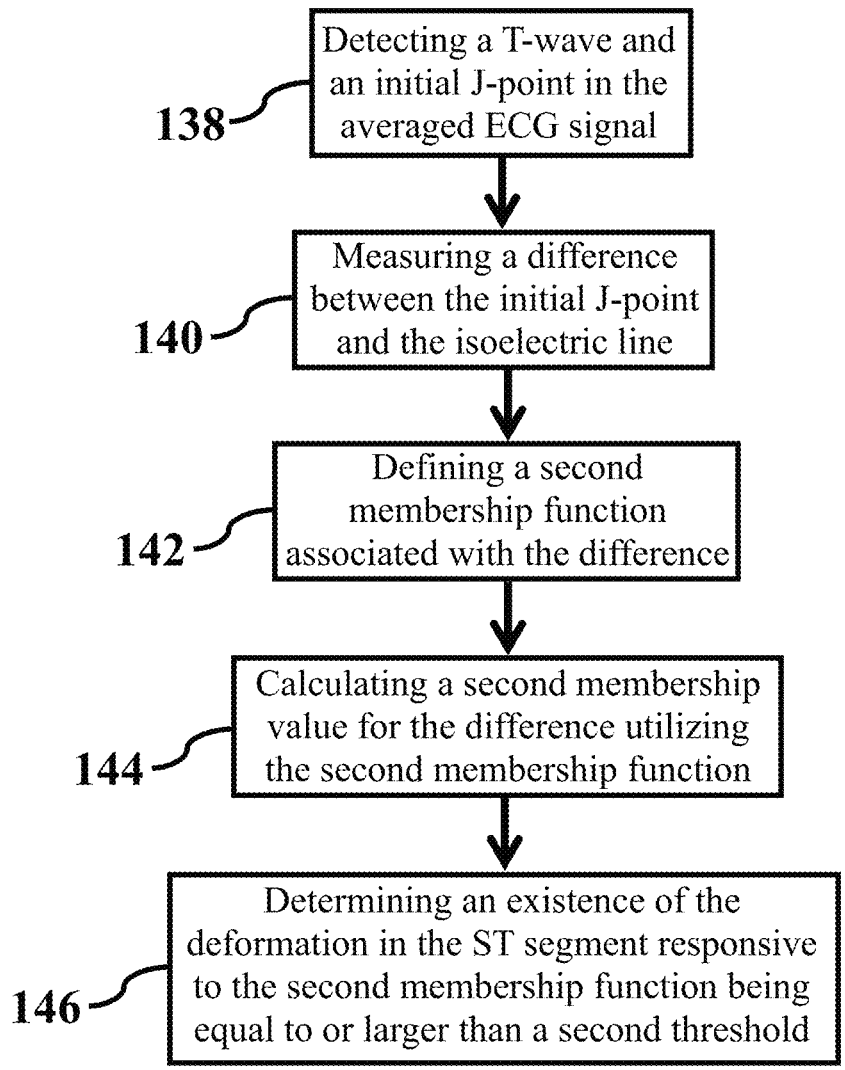
FIG. 1E shows a flowchart for detecting a deformation in an ST segment, consistent with one or more exemplary embodiments of the present disclosure.

Referring again to FIG. 1C, in an exemplary embodiment, step 124 may include detecting a deformation in ST segment 314. FIG. 1E shows a flowchart for detecting a deformation in an ST segment, consistent with one or more exemplary embodiments of the present disclosure. In an exemplary embodiment, step 124 may include detecting a T-wave and an initial J-point in averaged ECG signal 312 (step 138), measuring a difference between the initial J-point and the isoelectric line (step 140), defining a second membership function associated with the difference (step 142), calculating a second membership value for the difference utilizing the second membership function (step 144), and determining an existence of the deformation in the ST segment responsive to the second membership function being equal to or larger than a second threshold (step 146).

For further detail with respect to step 138, referring to FIG. 3E, an exemplary initial J-point may refer to an onset of ST segment 314. Therefore, in an exemplary embodiment, detecting the initial J-point may include extracting an onset J of ST segment 314. In an exemplary embodiment, detecting the T-wave may include detecting a (positive or negative) peak T of the T-wave by applying an SWT on averaged ECG signal 312, similar to detecting ST segment 314. In an exemplary embodiment, detecting the T-wave may include detecting a type of the T-wave. An exemplary type of the T-wave may include one of a normal T-wave and an inverted T-wave. In an exemplary embodiment, a normal T-wave may refer to a T-wave with a positive peak (i.e., a local maximum) and an inverted T-wave may refer to a T-wave with a negative peak (i.e., a local minimum). For example, the T-wave in averaged ECG signal 312 is a normal T-wave since it has a positive peak T.

In an exemplary embodiment, method 100 may further include determining a modified J-point on averaged ECG signal 312 responsive to detecting an inverted T-wave. An exemplary J-point modification may include modifying a location of the initial J-point on averaged ECG signal 312 by calculating a modified location $J_m$ for the modified J-point according to an operation defined by the following:

$$J_m = J_i - f_s/5 \qquad \text{Equation (1)}$$

where:

$J_i$ is a location of the initial J-point on averaged ECG signal 312, and $f_s$ is a sampling frequency of raw ECG signal 302.

In an exemplary embodiment, Equation (1) may be empirically obtained by relocating onset J at different modified locations and examining the impact of different relocations on the performance of method 100. In an exemplary embodiment, method 100 may further include replacing the initial J-point with the modified J-point prior to measuring the difference between the initial J-point and isoelectric line 316 in step 140 according to Equation (1).

In further detail regarding step 140, in an exemplary embodiment, measuring the difference between the initial J-point and isoelectric line 316 may include calculating an absolute value of averaged ECG signal 312 amplitude at onset J due to a zero amplitude of averaged ECG signal 312 on isoelectric line 316.

In further detail with regards to step 142, an exemplary second membership function may be selected similar to or different from first membership function 400. An exemplary second membership function may be utilized for fuzzy decision making over the difference between the initial J-point and isoelectric line 316. An exemplary second membership function may be obtained empirically by applying different functions on averaged ECG signal 312.

For further detail with respect to step 144, calculating the second membership value may include applying a measured value of an exemplary difference between the initial J-point and isoelectric line 316 to the second membership function and extracting a corresponding output of the second membership function as the second membership value for ST segment 314.

For further detail regarding step 146, in an exemplary embodiment, the second membership value may be compared with a second threshold. An exemplary second threshold may be set equal to about 0.8 based on examining different threshold values. In an exemplary embodiment, if the second membership value is equal to or larger than the second threshold, an existence of a deformation may be determined in ST segment 314.

Referring again to FIG. 1C, in an exemplary embodiment, step 126 may include detecting a plurality of abnormal morphologies in the plurality of averaged ECG signals. In an exemplary embodiment, detecting the plurality of abnormal morphologies may include detecting each of the plurality of abnormal morphologies in a respective averaged ECG signal of the plurality of averaged ECG signals.

Figure 1F:
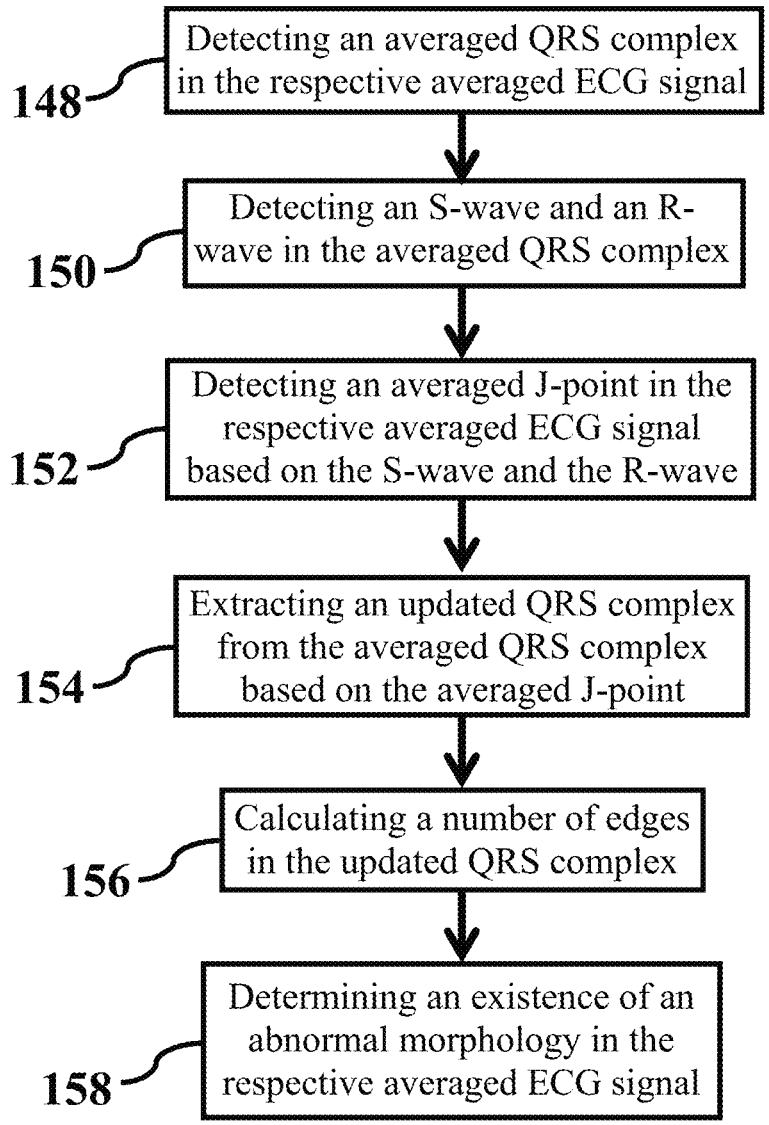
FIG. 1F shows a flowchart for detecting an abnormal morphology in a respective averaged ECG signal of a plurality of averaged ECG signals, consistent with one or more exemplary embodiments of the present disclosure.

FIG. 1F shows a flowchart for detecting an abnormal morphology in a respective averaged ECG signal of a plurality of averaged ECG signals, consistent with one or more exemplary embodiments of the present disclosure. In an exemplary embodiment, detecting each of the plurality of abnormal morphologies may include detecting an averaged QRS complex in the respective averaged ECG signal (step 148), detecting an S-wave and an R-wave in the averaged QRS complex (step 150), detecting an averaged J-point in the respective averaged ECG signal based on the S-wave and the R-wave (step 152), extracting an updated QRS complex from the averaged QRS complex based on the averaged J-point (step 154), calculating a number of edges in the updated QRS complex (step 156), and determining an existence of an abnormal morphology of the plurality of abnormal morphologies in the respective averaged ECG signal responsive to a temporal duration of the updated QRS complex being less than a temporal threshold and the number of edges being larger than a lower limit (step 158).

For further detail with respect to step 148, in an exemplary embodiment, each of the plurality of averaged ECG signals may include an averaged QRS complex. For example, referring again to FIG. 3E, averaged ECG signal 312 may include averaged QRS complex 318. In an exemplary embodiment, averaged QRS complex 318 may be detected by applying an SWT on averaged ECG signal 312 similar to detecting plurality of QRS complexes 310 in filtered ECG signal 308.

In further detail regarding step 150, in an exemplary embodiment, averaged QRS complex 318 may include an R-wave and an S-wave. An exemplary R-wave may include an exemplary edge R' and an exemplary S-wave may include an exemplary edge S'. Therefore, in an exemplary embodiment, each of the R-wave and an S-wave may be detected by detecting corresponding edges R' and S', respectively.

For further detail with regards to step 152, in an exemplary embodiment, detecting the averaged J-point may include calculating a coefficient cff according to an operation defined by the following:

$$cff = \frac{R_m - Iso}{S_m - Iso} \quad \text{Equation (2)}$$

where:
$R_m$ is a peak of the R-wave,
$S_m$ is a peak of the S-wave, and
Iso is an amplitude of the isoelectric line.

In an exemplary embodiment, Equation (2) may be empirically obtained for compensating the impact of different shapes of averaged QRS complex 318 on an accuracy of averaged J-point detection. In an exemplary embodiment, step 152 may further include setting a width W of a search range that may satisfy a set of conditions defined by the following:

$0.4f_s < W < 0.5f_s, cff \leq 0.1$      Condition (1a)

$0.3f_s < W < 0.4f_s, 0.1 < cff \leq 1.5$      Condition (1b)

$0.1f_s < W < 0.2f_s, cff > 1.5$      Condition (1c)

According to Condition (1a), in an exemplary embodiment, width W may be set equal to a value between $0.4f_s$ and $0.5f_s$ responsive to the coefficient cff being smaller than 0.1. According to Condition (1b), in an exemplary embodiment, width W may be set equal to a value between $0.3f_s$ and $0.4f_s$ responsive to the coefficient cff being between 0.1 and 1.5. According to Condition (1c), in an exemplary embodiment, width W may be set equal to a value between $0.1f_s$ and $0.2f_s$ responsive to the coefficient cff being larger than 1.5. In an exemplary embodiment, the averaged J-point may be obtained by finding a maximum amplitude of averaged ECG signal 312 in a range of $(t_s, t_s+W)$, where $t_s$ is a time instance corresponding to peak S' of the S-wave. In an exemplary embodiment, point on averaged ECG signal 312 with a maximum amplitude in the selected range may be selected as the averaged J-point. Consequently, in an exemplary embodiment, the initial J-point may be replaced with the averaged J-point.

For further detail with respect to step 154, after obtaining the averaged J-point, an exemplary updated QRS complex may be extracted from averaged QRS complex 318 utilizing the averaged J-point detected location. In an exemplary embodiment, the updated QRS complex may include updated Q, R, and S edges which may be detected on averaged ECG signal 312 similar to detecting corresponding edges of averaged QRS complex 318, except that the initial J-point location may be replaced with the averaged J-point.

In further detail regarding step 156, in an exemplary embodiment, the number of edges in the updated QRS complex may be calculated by counting a number of slope changes in the updated QRS complex. In an exemplary embodiment, a derivative of the updated QRS complex may be obtained and a number of zero-crossings of the derivative may indicate the number of slope changes, and hence, the number of edges of the updated QRS complex.

For further detail with regards to step 158, in an exemplary embodiment, the temporal threshold may be set to 120 ms, which may be an upper limit for a narrow QRS complex. Therefore, an exemplary precondition for detecting an abnormal morphology in averaged ECG signal 312 may be an existence of narrow QRS complex in averaged ECG signal 312. In an exemplary embodiment, the lower limit for the number of edges of the updated QRS complex may be set to 3. In an exemplary embodiment, the lower limit for the number of edges may be empirically selected by examining different ECG signals associated with CAD. Therefore, in an exemplary embodiment, an abnormal morphology may be detected in an averaged ECG signal with a narrow averaged QRS complex that may have more than 3 edges.

Figure 3F:
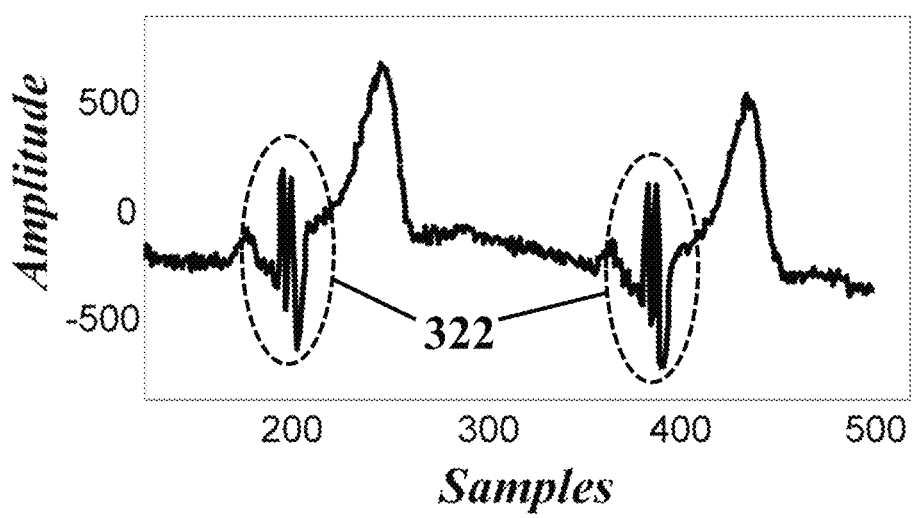
FIG. 3F shows a plurality of averaged ECG signals that include a plurality of abnormal morphologies, consistent with one or more exemplary embodiments of the present disclosure.

In an exemplary embodiment, detecting the plurality of abnormal morphologies may include detecting the plurality of abnormal morphologies in at least 25% of the plurality of averaged ECG signals. In an exemplary embodiment, the plurality of averaged ECG signals may include a duration of at least 10 minutes. Therefore, in an exemplary embodiment, if at least 25% of the plurality of averaged ECG signals which have a total duration of at least 10 minutes include abnormal morphologies, raw ECG signal 302 may be determined to contain abnormal morphologies. FIG. 3F shows a plurality of averaged ECG signals 320 that include a plurality of abnormal morphologies 322, consistent with one or more exemplary embodiments of the present disclosure.

Figure 5:
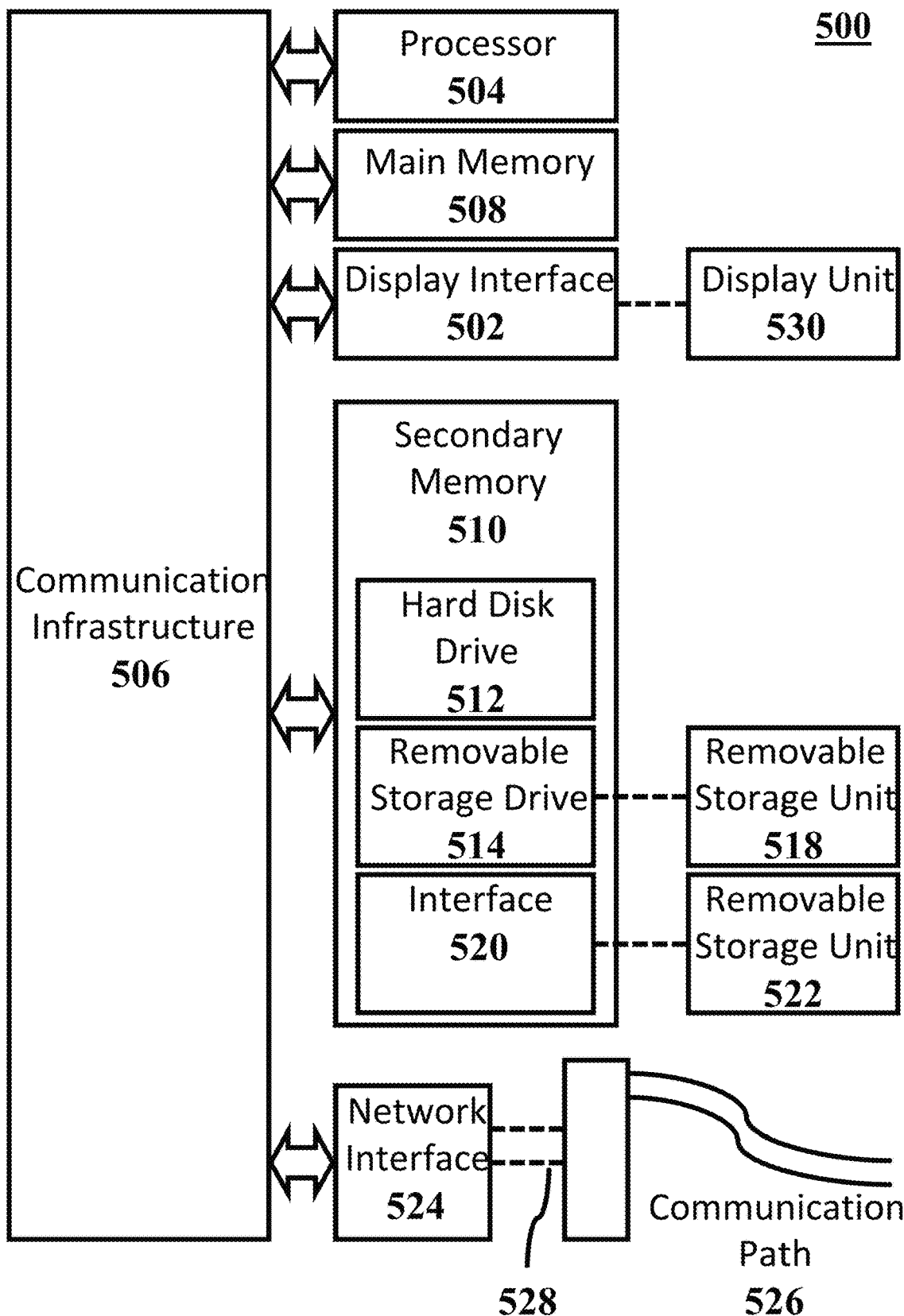
FIG. 5 shows a high-level functional block diagram of a computer system, consistent with one or more exemplary embodiments of the present disclosure.

FIG. 5 shows an example computer system 500 in which an embodiment of the present invention, or portions thereof, may be implemented as computer-readable code, consistent with exemplary embodiments of the present disclosure. For example, method 100 may be implemented in computer system 500 using hardware, software, firmware, tangible computer readable media having instructions stored thereon, or a combination thereof and may be implemented in one or more computer systems or other processing systems. Hardware, software, or any combination of such may embody any of the modules and components in FIGS. 1A-2.

If programmable logic is used, such logic may execute on a commercially available processing platform or a special purpose device. One ordinary skill in the art may appreciate that an embodiment of the disclosed subject matter can be practiced with various computer system configurations, including multi-core multiprocessor systems, minicomputers, mainframe computers, computers linked or clustered with distributed functions, as well as pervasive or miniature computers that may be embedded into virtually any device.

For instance, a computing device having at least one processor device and a memory may be used to implement the above-described embodiments. A processor device may be a single processor, a plurality of processors, or combinations thereof. Processor devices may have one or more processor "cores."

An embodiment of the invention is described in terms of this example computer system 500. After reading this description, it will become apparent to a person skilled in the relevant art how to implement the invention using other computer systems and/or computer architectures. Although operations may be described as a sequential process, some of the operations may in fact be performed in parallel, concurrently, and/or in a distributed environment, and with program code stored locally or remotely for access by single or multi-processor machines. In addition, in some embodiments the order of operations may be rearranged without departing from the spirit of the disclosed subject matter.

Processor device 504 may be a special purpose or a general-purpose processor device. As will be appreciated by persons skilled in the relevant art, processor device 504 may also be a single processor in a multi-core/multiprocessor system, such system operating alone, or in a cluster of computing devices operating in a cluster or server farm. Processor device 504 may be connected to a communication infrastructure 506, for example, a bus, message queue, network, or multi-core message-passing scheme.

In an exemplary embodiment, computer system 500 may include a display interface 502, for example a video connector, to transfer data to a display unit 530, for example, a monitor. Computer system 500 may also include a main memory 508, for example, random access memory (RAM), and may also include a secondary memory 510. Secondary memory 510 may include, for example, a hard disk drive 512, and a removable storage drive 514. Removable storage drive 514 may include a floppy disk drive, a magnetic tape drive, an optical disk drive, a flash memory, or the like. Removable storage drive 514 may read from and/or write to a removable storage unit 518 in a well-known manner. Removable storage unit 518 may include a floppy disk, a magnetic tape, an optical disk, etc., which may be read by and written to by removable storage drive 514. As will be appreciated by persons skilled in the relevant art, removable storage unit 518 may include a computer usable storage medium having stored therein computer software and/or data.

In alternative implementations, secondary memory 510 may include other similar means for allowing computer programs or other instructions to be loaded into computer system 500. Such means may include, for example, a removable storage unit 522 and an interface 520. Examples of such means may include a program cartridge and cartridge interface (such as that found in video game devices), a removable memory chip (such as an EPROM, or PROM) and associated socket, and other removable storage units 522 and interfaces 520 which allow software and data to be transferred from removable storage unit 522 to computer system 500.

Computer system 500 may also include a communications interface 524.

Communications interface 524 allows software and data to be transferred between computer system 500 and external devices. Communications interface 524 may include a modem, a network interface (such as an Ethernet card), a communications port, a PCMCIA slot and card, or the like. Software and data transferred via communications interface 524 may be in the form of signals, which may be electronic, electromagnetic, optical, or other signals capable of being received by communications interface 524. These signals may be provided to communications interface 524 via a communications path 526. Communications path 526 carries signals and may be implemented using wire or cable, fiber optics, a phone line, a cellular phone link, an RF link or other communications channels.

In this document, the terms "computer program medium" and "computer usable medium" are used to generally refer to media such as removable storage unit 518, removable storage unit 522, and a hard disk installed in hard disk drive 512. Computer program medium and computer usable medium may also refer to memories, such as main memory 508 and secondary memory 510, which may be memory semiconductors (e.g. DRAMs, etc.).

Computer programs (also called computer control logic) are stored in main memory 508 and/or secondary memory 510. Computer programs may also be received via communications interface 524. Such computer programs, when executed, enable computer system 500 to implement different embodiments of the present disclosure as discussed herein. In particular, the computer programs, when executed, enable processor device 504 to implement the processes of the present disclosure, such as the operations in method 100 illustrated by flowcharts of FIGS. 1A-1F discussed above. Accordingly, such computer programs represent controllers of computer system 500. Where an exemplary embodiment of method 100 is implemented using software, the software may be stored in a computer program product and loaded into computer system 500 using removable storage drive 514, interface 520, and hard disk drive 512, or communications interface 524.

Embodiments of the present disclosure also may be directed to computer program products including software stored on any computer useable medium. Such software, when executed in one or more data processing device, causes a data processing device to operate as described herein. An embodiment of the present disclosure may employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, and optical storage devices, MEMS, nano-technological storage device, etc.).

The embodiments have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

EXAMPLE

In this example, an implementation of method 100 for CAD detection is demonstrated. Four specific datasets were collected from different cohorts of cardiac patients containing a total of 300 patients in a period of 72 months. The four aforementioned cohorts of patients consist of 200 patients from DAY General Hospital in Tehran, Iran, 54 patients from CHUV hospital in Lausanne, Switzerland, 20 patients from Masih Daneshvari Hospital in Tehran, Iran, and 26 CAD-cardiac electrophysiolocal patients from DAY General Hospital in Tehran, Iran. Also 50 individuals were selected either from other cardiac patients with no apparent symptom of coronary artery diseases, or from some young and apparently healthy volunteers as the control (Healthy) group.

Raw ECG signals were obtained before undergoing coronary angiography for a duration of approximately 10 minutes with three-lead ambulatory Holter ECG unit. For each of the cohorts of the CAD patients, coronary angiography was defined as the gold standard.

The anticipated evaluation population included a group of individuals of different ages from both sexes. For purpose of evaluation, such group of participating patients and individuals had no background of coronary angiography, no background of percutaneous transluminal coronary angioplasty (PTCA) or coronary artery bypass grafting (CABG), no recorded history of CADs and existing ambulatory holter ECG recording (at least for 10 minutes) taken at the hospital.

Patients who have such records were eliminated from population. Therefore, the population were divided into the two main groups of CAD patients and healthy individuals or the control group. The group of CAD patents included the four specific subgroups including a group of patients who had experienced chest pain and were referred to the CHUV, Day and Masih Daneshvari hospitals or cardiologist offices at these centers and based on the initial findings such as Troponin test, ECG interpretation or their clinical symptoms, were suspected of coronary artery blockage (coronary artery disease). All these patients were prescribed for angiography. This group of patients were divided into the four main subgroups including patients who definitely had CAD and suffered from acute CAD and had to undergo CABG, patients who definitely had CAD and suffered from acute CAD, however, the quality of the artery occlusion was such that they did not require CABG, and therefore, the act of placing a stent or balloon in vessels, or PTCA was prescribed for them, and patients who had angiography and suffered from coronary artery occlusion, however, they did not need invasive therapy, on the other hand, the severity of occlusion was not insignificant and therefore had not been ignored and thus, medical follow up was prescribed for this group, and finally, individuals who had undergone coronary angiography and their coronary occlusion was negligible, hence they were considered normal population.

The second group, known as the healthy individuals or the control group, included the other cardiac patients with no apparent symptom of coronary artery diseases, and some young and apparently healthy volunteer students.

The four cohorts of patients included the cohort of cardiac patients from Day general hospital in Tehran, Iran, that included a total of 200 patients, cohort of the cardiac patients from Masih Daneshvari hospital in Tehran, Iran, that included 20 patients, the cohort of the cardiac patients from CHUV hospital in Lausanne, Switzerland, that included a total of 54 patients, and the cohort of the cardiac electrophysiological CAD patients from DAY general hospital in Tehran, that included a total of 25 subjects.

The latter cohort included a group of electrophysiological patients having either a similar sign or symptom of the CAD, or having ECG signals resembling known criteria of CAD. Thus, these patients might incorrectly be diagnosed as CAD cases. This group of patients usually suffer from Left Bundle Branch Block (LBBB) or Right Bundle Branch Block (RBBB) arrhythmia. The Electrocardiogram (ECG) signals from a total of 25 patients of this cohort was obtained. Since most of these patients had presented with either typical or atypical CAD clinical symptoms, they had undergone coronary angiography for a superior assessment. Evaluation of method 100 with such particular cohort of patient may be essential because it may be so effective to reduce a false alarm and consequently increase negative predictive value accuracy. In this example, the presence of left or right bundle branch block arrhythmias is estimated using 3 leads of ambulatory Holter ECGs, and then, the left and right bundle branch blocks are separated from each other. Thereafter, CAD cases with bundle branch block arrhythmias are diagnosed from normal coronary bundle branch subjects.

Technical specifications of the ECG recorder used for data gathering process are as follows:

Number of ECG channels: 3 time synchronized differential inputs

Input resistance: 10 M Ohm/22 nF

Sensitivity: ±7 mV

DC stability: ±300 mV

Frequency response: 0.05-55 Hz

Resolution: 12 Bit

Sample rate: 200 Hz per ECG channel

An evaluation of method 100 with the available cohorts of cardiac patients was performed according to the comparison with the available ten-minute Holter from the normal coronary individuals. The obtained results are shown in TABLE 1.

TABLE 1

| Database | Day general hospital electrophysiological database | Day general hospital database | CHUV hospital database | Masih Daneshvari hospital database |
|---|---|---|---|---|
| Sensitivity (%) | 88.9% | 90.91% | 87.03% | 84.6% |
| Positive predictive values (%) | 81.25% | 95.24% | 94% | 88% |
| Specificity (%) | 72.7% | 92.31% | 94.23% | 94.23% |
| Negative predictive values (%) | 92.8% | 85.71% | 87.5% | 92.45% |
| Average Accuracy (%) | 84% | 91.43% | 90.56% | 91.02% |

While the foregoing has described what may be considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A computer-implemented method for non-invasive detection of coronary artery disease (CAD), the method comprising:
   acquiring a raw electrocardiography (ECG) signal associated with a patient;
   generating, utilizing one or more processors, a denoised ECG signal by applying a first wavelet transform on the raw ECG signal;
   generating, utilizing the one or more processors, an artifact-free ECG signal by applying a second wavelet transform on the denoised ECG signal;
   generating, utilizing the one or more processors, a filtered ECG signal by applying a finite impulse response (FIR) filter on the artifact-free ECG signal, the filtered ECG signal comprising a plurality of QRS complexes;
   extracting, utilizing the one or more processors, an averaged ECG signal of a plurality of averaged ECG signals from the filtered ECG signal;
   detecting, utilizing the one or more processors, an ST segment and an isoelectric line in the averaged ECG signal;
   determining, utilizing the one or more processors, an existence of CAD in the patient responsive to detecting at least one of a plurality of CAD detection conditions, detecting the at least one of a plurality of CAD detection conditions comprising:

detecting one of a depression or an elevation in the ST segment with respect to the isoelectric line;
detecting a deformation in the ST segment; or
detecting a plurality of abnormal morphologies in the plurality of averaged ECG signals; and
determining, utilizing the one or more processors, a non-existence of CAD responsive to not detecting the at least one of the plurality of CAD detection conditions.

2. The method of claim 1, wherein acquiring the raw ECG signal comprises:
placing three precordial ECG leads on a chest of the patient; and
recording the raw ECG signal from the three precordial ECG leads.

3. The method of claim 1, wherein extracting the averaged ECG signal comprises extracting five consecutive QRS complexes of the plurality of QRS complexes from the filtered ECG signal.

4. The method of claim 1, wherein detecting the one of the depression or the elevation in the ST segment comprises:
measuring variations of the ST segment with respect to the isoelectric line;
defining a first membership function associated with the variations of the ST segment;
calculating a first membership value for the ST segment utilizing the first membership function; and
determining an existence of the one of the depression or the elevation in the ST segment responsive to the first membership value being equal to or higher than a first threshold.

5. The method of claim 4, wherein detecting the deformation in the ST segment comprises:
detecting a T-wave and an initial J-point in the averaged ECG signal;
measuring a difference between the initial J-point and the isoelectric line;
defining a second membership function associated with the difference;
calculating a second membership value for the difference utilizing the second membership function; and
determining an existence of the deformation in the ST segment responsive to the second membership function being equal to or larger than a second threshold.

6. The method of claim 5, further comprising:
detecting a type of the T-wave comprising one of a normal T-wave and an inverted T-wave;
determining a modified J-point on the averaged ECG signal responsive to detecting the inverted T-wave by modifying a location of the initial J-point on the averaged ECG signal; and
replacing the initial J-point with the modified J-point prior to measuring the difference between the initial J-point and the isoelectric line.

7. The method of claim 6, wherein modifying the location of the initial J-point comprises calculating a modified location $J_m$ for the modified J-point according to an operation defined by the following:

$$J_m = J_i - f_s/5,$$

where:
$J_i$ is a location of the initial J-point on averaged ECG signal, and
$f_s$ is a sampling frequency of the raw ECG signal.

8. The method of claim 1, wherein detecting the plurality of abnormal morphologies comprises detecting each of the plurality of abnormal morphologies in a respective averaged ECG signal of the plurality of averaged ECG signals, detecting each of the plurality of abnormal morphologies comprising:
detecting an averaged QRS complex in the respective averaged ECG signal;
detecting an S-wave and an R-wave in the averaged QRS complex;
detecting an averaged J-point in the respective averaged ECG signal based on the S-wave and the R-wave;
extracting an updated QRS complex from the averaged QRS complex based on the averaged J-point;
calculating a number of edges in the updated QRS complex; and
determining an existence of an abnormal morphology of the plurality of abnormal morphologies in the respective averaged ECG signal responsive to:
a temporal duration of the updated QRS complex being less than a temporal threshold; and
the number of edges being larger than a lower limit.

9. The method of claim 8, wherein detecting the averaged J-point comprises:
calculating a coefficient cff according to an operation defined by the following:

$$cff = \frac{R_m - Iso}{S_m - Iso},$$

where:
$R_m$ is a peak of the R-wave,
$S_m$, is a peak of the S-wave, and
Iso is an amplitude of the isoelectric line;
setting a width W of a search range equal to a value between $0.4f_s$ and $0.5f_s$ responsive to the coefficient cff being smaller than 0.1;
setting a width W of a search range equal to a value between $0.3f_s$ and $0.4f_s$ responsive to the coefficient cff being between 0.1 and 1.5;
setting a width W of a search range equal to a value between $0.1f_s$ and $0.2f_s$ responsive to the coefficient cff being larger than 1.5; and
obtaining the averaged J-point by finding a maximum amplitude of the respective averaged ECG signal in a range of $(t_s, t_s+W)$, where $t_s$ is a time instance corresponding to the peak of the S-wave.

10. The method of claim 1, wherein detecting the plurality of abnormal morphologies comprises detecting the plurality of abnormal morphologies in at least 25% of the plurality of averaged ECG signals, the plurality of averaged ECG signals comprising a duration of at least 10 minutes.

11. A system for non-invasive detection of coronary artery disease (CAD), the system comprising:
a plurality of precordial electrocardiography (ECG) leads configured to be placed on a chest of a patient and acquire a raw ECG signal from the patient;
an ECG recorder configured to record the raw ECG signal from the plurality of precordial ECG leads;
a memory having processor-readable instructions stored therein; and
one or more processors configured to access the memory and execute the processor-readable instructions, which, when executed by the one or more processors configures the one or more processors to perform a method, the method comprising:

receiving the raw ECG signal from the ECG recorder;
generating a denoised ECG signal by applying a first wavelet transform on the raw ECG signal;
generating an artifact-free ECG signal by applying a second wavelet transform on the denoised ECG signal;
generating a filtered ECG signal by applying a finite impulse response (FIR) filter on the artifact-free ECG signal, the filtered ECG signal comprising a plurality of QRS complexes;
extracting an averaged ECG signal of a plurality of averaged ECG signals from the filtered ECG signal;
detecting an ST segment and an isoelectric line in the averaged ECG signal;
determining an existence of CAD in the patient responsive to detecting at least one of a plurality of CAD detection conditions, detecting the at least one of a plurality of CAD detection conditions comprising:
  detecting one of a depression or an elevation in the ST segment with respect to the isoelectric line;
  detecting a deformation in the ST segment; or
  detecting a plurality of abnormal morphologies in the plurality of averaged ECG signals; and
determining a non-existence of CAD responsive to not detecting the at least one of the plurality of CAD detection conditions.

12. The system of claim 11, wherein the plurality of ECG leads comprise three precordial ECG leads configured to be placed on a chest of the patient.

13. The system of claim 11, wherein extracting the averaged ECG signal comprises extracting five consecutive QRS complexes of the plurality of QRS complexes from the filtered ECG signal.

14. The system of claim 11, wherein detecting the one of the depression or the elevation in the ST segment comprises:
measuring variations of the ST segment with respect to the isoelectric line;
defining a first membership function associated with the variations of the ST segment;
calculating a first membership value for the ST segment utilizing the first membership function; and
determining an existence of the one of the depression or the elevation in the ST segment responsive to the first membership value being equal to or higher than a first threshold.

15. The system of claim 11, wherein detecting the deformation in the ST segment comprises:
detecting a T-wave and an initial J-point in the averaged ECG signal;
measuring a difference between the initial J-point and the isoelectric line;
defining a second membership function associated with the difference;
calculating a second membership value for the difference utilizing the second membership function; and
determining an existence of the deformation in the ST segment responsive to the second membership function being equal to or larger than a second threshold.

16. The system of claim 15, wherein detecting the deformation in the ST segment further comprises:
detecting a type of the T-wave comprising one of a normal T-wave and an inverted T-wave;
determining a modified J-point on the averaged ECG signal responsive to detecting the inverted T-wave by modifying a location of the initial J-point on the averaged ECG signal; and
replacing the initial J-point with the modified J-point prior to measuring the difference between the initial J-point and the isoelectric line.

17. The system of claim 16, wherein modifying the location of the initial J-point comprises calculating a modified location $J_m$ for the modified J-point according to an operation defined by the following:

$$J_m = J_i - f_s/5,$$

where:
  $J_i$ is a location of the initial J-point on averaged ECG signal, and
  $f_s$ is a sampling frequency of raw ECG signal.

18. The system of claim 11, wherein detecting the plurality of abnormal morphologies comprises detecting each of the plurality of abnormal morphologies in a respective averaged ECG signal of the plurality of averaged ECG signals, detecting each of the plurality of abnormal morphologies comprising:
detecting an averaged QRS complex in the respective averaged ECG signal;
detecting an S-wave and an R-wave in the averaged QRS complex;
detecting an averaged J-point in the respective averaged ECG signal based on the S-wave and the R-wave;
extracting an updated QRS complex from the averaged QRS complex based on the averaged J-point;
calculating a number of edges in the updated QRS complex; and
determining an existence of an abnormal morphology of the plurality of abnormal morphologies in the respective averaged ECG signal responsive to:
  a temporal duration of the updated QRS complex being less than a temporal threshold; and
  the number of edges being larger than a lower limit.

19. The system of claim 18, wherein detecting the averaged J-point comprises:
calculating a coefficient cff according to an operation defined by the following:

$$cff = \frac{R_m - Iso}{S_m - Iso};$$

where:
  $R_m$ is a peak of the R-wave,
  $S_m$ is a peak of the S-wave, and
  Iso is an amplitude of the isoelectric line;
setting a width W of a search range equal to a value between $0.4f_s$ and $0.5f_s$ responsive to the coefficient cff being smaller than 0.1;
setting a width W of a search range equal to a value between $0.3f_s$ and $0.4f_s$ responsive to the coefficient cff being between 0.1 and 1.5;
setting a width W of a search range equal to a value between $0.1f_s$ and $0.2f_s$ responsive to the coefficient cff being larger than 1.5; and
obtaining the averaged J-point by finding a maximum amplitude of the respective averaged ECG signal in a range of $(t_s, t_s+W)$, where $t_s$ is a time instance corresponding to the peak of the S-wave.

20. The system of claim 11, wherein detecting the plurality of abnormal morphologies comprises detecting the plurality of abnormal morphologies in at least 25% of the plurality of averaged ECG signals, the plurality of averaged ECG signals comprising a duration of at least 10 minutes.

* * * * *